United States Patent [19]

Plummer et al.

[11] Patent Number: 4,592,905

[45] Date of Patent: Jun. 3, 1986

[54] CONVERSION OF HYDROGEN SULFIDE TO SULFUR AND HYDROGEN

[75] Inventors: Mark A. Plummer; Phillip M. Beazley, both of Littleton, Colo.

[73] Assignee: Marathon Oil Company, Findlay, Ohio

[21] Appl. No.: 691,232

[22] Filed: Jan. 14, 1985

[51] Int. Cl.$^4$ .................. B01D 53/14; C01B 17/05; C01B 3/22

[52] U.S. Cl. .................. 423/573 R; 260/369; 423/648 R; 423/226

[58] Field of Search .................. 423/573 R, 648 R; 260/369, 376

[56] References Cited

U.S. PATENT DOCUMENTS

| | | | |
|---|---|---|---|
| 2,693,998 | 11/1954 | Kopsch | 23/207 |
| 2,819,950 | 1/1958 | Patton | 423/573 R |
| 2,997,439 | 8/1961 | Nicklin et al. | 423/573 R |
| 3,004,831 | 10/1961 | Hungerford et al. | 23/207 |
| 3,035,889 | 5/1962 | Nicklin et al. | 23/2 |
| 3,126,257 | 3/1964 | Kunowski et al. | 23/207 |
| 3,311,453 | 3/1967 | Lusby | 423/579 |
| 3,372,990 | 3/1968 | Charret | 23/207 |
| 3,752,885 | 8/1973 | Liebert et al. | 423/588 |
| 3,912,766 | 10/1975 | Logan et al. | 260/369 |
| 3,923,966 | 12/1975 | Vaughan | 423/573 R |
| 3,937,795 | 2/1976 | Hasebe | 423/573 |
| 3,972,989 | 8/1976 | Fenton et al. | 423/573 |
| 4,002,727 | 1/1977 | Sonoda et al. | 423/573 R |
| 4,060,594 | 11/1977 | Fenton et al. | 423/573 R |

FOREIGN PATENT DOCUMENTS 1173173  12/1969  United Kingdom .............. 423/226

Primary Examiner—John Doll
Assistant Examiner—Jeffrey E. Russel
Attorney, Agent, or Firm—Jack L. Hummel; Rodney F. Brown

[57] ABSTRACT

A hydrogen sulfide gas is converted to sulfur and hydrogen gas by reacting the hydrogen sulfide and with an anthraquinone dissolved in a polar hydrocarbon solvent. The hydrogen sulfide reacts with the anthraquinone to produce sulfur and an anthrahydroquinone. Sulfur is then removed from the solvent. The anthraquinone is regenerated from the anthrahydroquinone yielding hydrogen gas. The anthraquinone is recycled with the solvent to the reaction.

28 Claims, No Drawings

CONVERSION OF HYDROGEN SULFIDE TO SULFUR AND HYDROGEN

DESCRIPTION

BACKGROUND OF THE INVENTION

1. Technical Field

The invention relates to a process for converting hydrogen sulfide to sulfur and hydrogen and, more specifically, to a process for reacting hydrogen sulfide gas with an anthraquinone, yielding sulfur and the corresponding anthrahydroquinone which is then converted back to the anthraquinone while releasing hydrogen gas.

2. Background Art

Many processes related to the petroleum industry generate gaseous by-products containing hydrogen sulfide, by itself or in a mixture with other gases, such as carbon dioxide. The by-product gas is generally oxidized to obtain sulfur. A common oxidation process is the Claus process, which oxidizes hydrogen sulfide directly with air to produce sulfur and water. One disadvantage of the Claus process is that it requires expensive pretreatment of the feed gas if carbon dioxide is present in high concentrations. At least a portion of the carbon dioxide must be removed from the by-product gas by pretreatment before oxidizing the hydrogen sulfide to maintain the efficiency of the oxidation process. Other shortcomings of the Claus process are that it operates at high temperatures, it requires exacting process control over the ratio of oxygen to hydrogen sulfide in the feed, and the annual maintenance costs for the Claus process are typically 20 percent of the initial capital investment. Finally, the sulfur content of Claus process tail gas released to the atmosphere is generally too high to meet stringent environmental regulations. To comply with these regulations, it is necessary to add more Claus stages and/or employ a separate tail gas clean-up process at great expense.

The art is rife with modified Claus processes and other hydrogen sulfide oxidation processes which attempt to overcome the deficiencies of the basic Claus process. U.S. Pat. No. 2,819,950 to Patton converts hydrogen sulfide to sulfur and hydrogen by means of a quinone having an oxidation potential of at least 0.2 volts, which excludes antraquinones. The reaction is carried out in an acidic solution, comprising water, aqueous alcohol or other hydrophilic solvent, to produce sulfur and hydroquinone. The hydroquinone is electrolyzed in solution to obtain quinone and hydrogen. U.S. Pat. No. 3,311,453 to Lusby converts hydrogen sulfide into sulfur and either hydrogen peroxide or oxygen by means of an anthraquinone disulfonate dissolved in water. U.S. Pat. No. 3,923,966 to Vaughan reacts hydrogen sulfide with an anthraquinone in an organic solvent in the presence of an amine catalyst to produce elemental sulfur and hydrogen peroxide.

The above-cited patents are all burdened by strict process controls needed to regenerate the hydroquinone. A simpler process is needed for treating hydrogen sulfide gas and, more specifically, a process is needed which decomposes a hydrogen sulfide gas by means of a quinone to recover sulfur and hydrogen in a simple, cost-effective and environmentally acceptable manner.

SUMMARY OF THE INVENTION

The present invention is a process for contacting a hydrogen sulfide gas with an anthraquinone dissolved in a polar organic solvent. The resulting reaction yields sulfur and the corresponding anthrahydroquinone. The sulfur precipitates from the solution and is recovered as a product while the remaining anthrahydroquinone solution is fed to a dehydrogenation reactor. The anthrahydroquinone is thermally or catalytically regenerated therein producing the initial anthraquinone form in solution and releasing hydrogen gas. The anthraquinone solution is recycled back to the hydrogen sulfide reactor and the hydrogen is recovered as a product.

The present process avoids the inherent problems of the Claus process which uses air oxidation to decompose the hydrogen sulfide to sulfur and water. The process does not require expensive pretreatment of the feed gas because very little of the unreactive constituents in the feed gas is dissolved in the reaction solvent. The process does not produce a sulfur-containing tail gas. Process controls are less costly than the Claus process because the present process is less sensitive to variations in reaction conditions and feed gas composition. Finally hydrogen is advantageously produced which can be used for fuel desulfurization, sold as a chemical, or burned to provide a high temperature heat source.

DESCRIPTION OF THE PREFERRED EMBODIMENTS

According to the present invention, a feed gas, containing hydrogen sulfide ($H_2S$), and an anthraquinone, which is dissolved in a polar organic solvent, are contacted in an $H_2S$ reactor. Upon contact, the solvent preferentially solubilizes only the $H_2S$ portion of the feed gas, although the solvent may also solubilize small amounts of carbon dioxide ($CO_2$) or other unreactive compounds, if they are present in the feed gas. This solution is referred to as the "reaction solution" herein. The reaction solution is maintained in the reactor at a temperature from about 30° to about 80° C. and at an $H_2S$ partial pressure from about 600 to about 1200 kPa for a time sufficient to convert the $H_2S$ and anthraquinone to sulfur and anthrahydroquinone. This is generally from about 0.1 to 3 hours, depending on the polarity of the solvent. The anthraquinone concentration in the reaction solution is not critical, although a higher concentration favors an increased reaction rate, which is preferred. The upper concentration limit of anthraquinone is its saturation point in the particular solvent at the reaction temperature.

The insoluble sulfur, e.g. $S_8$ or other forms of polymerized sulfur, is withdrawn from the reactor as a precipitate in the reaction solution. The sulfur is separated from the solution by filtration, centrifugation, or other means known in the art. It is then dried or melted to a liquid form.

After removal of the sulfur product, the solution withdrawn from the $H_2S$ reactor contains anthrahydroquinone, solvent, and any unreacted compounds from the feed gas. This solution is heated to the dehydrogenation temperature of from about 200° to about 350° C. at the dehydrogenation pressure of from about atmospheric to about 1000 kPa and fed to a flash tank. Substantially all unreacted feed gas constituents, including $H_2S$ and $CO_2$, are removed from the solution in the flash tank for recycle to the $H_2S$ reactor. The solution is withdrawn from the flash tank and fed to a dehydrogenation reactor where the anthrahydroquinone is catalytically or thermally converted to anthraquinone and hydrogen gas ($H_2$) under the temperature and pressure conditions stated above. The residence time in the dehydrogenation reactor is generally from about 1 to about 10 minutes (volume catalyst/volume feed/minute). The solution withdrawn from the dehydrogenation reactor contains the anthraquinone in its initial form dissolved in the polar organic solvent. The solution is recycled to the $H_2S$ reactor and the $H_2$ is recovered as a commercial product.

Although the mechanism by which the $H_2S$ is converted to sulfur is not certain, it is believed that two chemical reactions occur. The first is an $H_2S$-anthraquinone reaction, a two step reaction. The $H_2S$ first contacts the solvent to form a quaternary ion complex which in turn reacts with the anthraquinone to yield elemental sulfur and the corresponding anthrahydroquinone. The second reaction is the sulfur polymerization reaction, which polymerizes elemental sulfur to polymerized sulfur. The polymerized sulfur then precipitates out of solution.

A primary parameter controlling both the $H_2S$-anthraquinone and sulfur polymerization reactions is the choice of solvent in the reaction solution. Increasing solvent polarity has two favorable effects on these reactions: (1) the extent of reaction increases; and (2) the total time for the $H_2S$-anthraquinone and sulfur polymerization reactions decreases. Preferred solvents are organic compounds which have a high polarity, i.e., greater than about 3 Debye units, yet remain stable at dehydrogenation temperatures. These solvents include nitrobenzene, 2-pyrrolidone, n,n-dimethylacetamide, 1,3-dimethyl urea and n,n-dimethylformamide. The most preferred solvent is n-methyl-2-pyrrolidone (NMP).

Other important process parameters are the choice of anthraquinone as well as the process temperature and pressure. Optimization of the process requires balancing competing factors. For example, each step of the $H_2S$-anthraquinone reaction optimally proceeds within a different temperature range. Quaternary ion complex formation is favored at lower temperature and anthraquinone to anthrahydroquinone conversion is favored at higher temperature. An optimal temperature generally compromises these two factors. With respect to pressure, increased $H_2S$ partial pressure increases both quaternary ion complex formation and desirably higher anthraquinone conversion. However, a large quaternary ion complex concentration undesirably increases the sulfur polymerization time.

In general, a preferred anthraquinone maximizes $H_2S$ conversion to polymerized sulfur. Choice of the anthraquinone is based on such properties as the solubility of anthraquinone in the organic solvent and the electronegativity of the anthraquinone. Solubility is a function of the groups substituted on the anthraquinone. For example, alkyl anthraquinones have much higher solubilities than sulfonated anthraquinones. Likewise, electronegativity is a function of the anthraquinone substituents. Useful anthraquinones are ethyl anthraquinone and t-butyl anthraquinone because they have relatively high electronegativities, enabling them to more effectively attract positive hydrogen ions from the quaternary ion complex and increase the conversion of the anthraquinone to the corresponding anthrahydroquinone.

Catalytic dehydrogenation of the anthrahydroquinone is a function of catalyst type and dehydrogenation temperature. Under improperly selected conditions, the anthrahydroquinone may undesirably be converted to the corresponding anthrone. Although the anthrone may be converted back to the anthraquinone and water on contact with oxygen, the preferred catalyst reduces the need to do so by maximizing anthrahydroquinone conversion to the corresponding anthraquinone at the lowest temperature. Both the catalyst metal and support influence catalyst performance. More basic catalyst supports such as silica, alumina, or magnesium oxide minimize anthrone production compared to more acidic supports such as a combined silica-alumina support. Catalyst metals which are electron attracting or p-type conductors also minimize anthrone production and correspondingly maximize anthraquinone production.

Preferred embodiments of the invention are set forth below by example but are not to be construed as limiting the scope of the invention. Examples 1–6 describe selection of a solvent and an anthraquinone and optimization of $H_2S$-anthraquinone reaction parameters.

EXAMPLE 1

$H_2S$ and t-butyl anthraquinone are dissolved in several solvents. They are then reacted in the $H_2S$ reactor at optimum conditions to determine which combination of reactants and solvents yields the greatest conversion of anthraquinone to anthrahydroquinone. The results are set forth in Table 1 below.

TABLE 1

| Solvent | Temp (°C.) | $H_2S$ Partial Pressure (kPa) | Polarity (Debye units) | % Conversion |
|---|---|---|---|---|
| Diethylamine | 37 | 83 | 1.1 | 0 |
| Quinoline | 44–55 | 83–1048 | 2.2 | 0 |
| Acetophenone | 43–56 | 83–1117 | 3.0 | 0 |
| 2-Pyrrolidone | 54 | 83 | 3.6 | 7 |
| n,n-Dimethylformamide | 52–63 | 83–1124 | 3.9 | 40 |
| n-Methyl-2-Pyrrolidone (NMP) | 57 | 1082 | 4.1 | 53 |
| 40% 1,3 Dimethyl Urea - 60% NMP | 58 | 979 | 4.4 | 65 |
| Hexamethyl Phosphoric Triamide | 54 | 83 | 5.5 | 78 |

Table 1 indicates that only solvents having a polarity above about 3 Debye units can be used for conversion of t-butyl anthraquinone to the corresponding anthrahydroquinone. The data also show that conversion increases as solvent polarity increases.

EXAMPLE 2

$H_2S$ and t-butyl anthraquinone are dissolved in two different solvents to determine the relationship between reaction time and solvent polarity. The reactions are carried out at temperatures from 54° to 60° C. and at $H_2S$ partial pressures from 965 to 1117 kPa. The reaction time using pure NMP solvent, having a polarity of 4.1 Debye units, is 2.5 hours while the reaction time using a solvent mixture comprised of 60 wt.% NMP and 40 wt.% 1,3 dimethyl urea, having a polarity of 4.4 Debye units, is only 0.5 hours. As solvent polarity increases, reaction time appears to decrease.

EXAMPLE 3

The conversion of t-butyl anthraquinone to t-butyl anthrahydroquinone is maximized as a function of temperature. The reactions are carried out at several temperatures for 2.5 hours at $H_2S$ partial pressures between 965 to 1089 kPa in NMP solvent. The results are shown in Table 2 below.

TABLE 2

| Temperature (°C.) | % Conversion |
| --- | --- |
| 45 | 44 |
| 52 | 49 |
| 56 | 53 |
| 57 | 52 |
| 59 | 53 |
| 63 | 50 |
| 69 | 44 |
| 76 | 38 |

Optimum temperature for maximum t-butyl anthraquinone conversion to t-butyl anthrahydroquinone in NMP solvent is about 56° to 59° C.

EXAMPLE 4

The conversion of t-butyl anthraquinone to the corresponding anthrahydroquinone is maximized as a function of $H_2S$ partial pressure. The reactions are carried out at several $H_2S$ partial pressures for 2 to 2.75 hours at a temperature between 56° and 59° C. in NMP solvent. The results are listed in Table 3 below.

TABLE 3

| $H_2S$ Partial Pressure (kPa) | % Conversion |
| --- | --- |
| 83 | 10 |
| 634 | 50 |
| 772 | 57 |
| 979 | 62 |
| 1048 | 57 |
| 1082 | 51 |
| 1102 | 48 |

Optimum $H_2S$ partial pressure for maximum t-bytyl anthraquinone conversion to t-butyl anthrahydroquinone is about 980 kPa.

EXAMPLE 5

$H_2S$ and ethyl anthraquinone are dissolved in n,n-dimethylformamide solvent and reacted at 52° C. and an $H_2S$ partial pressure of 83 kPa for 2.5 hours. About 34% of the ethyl anthraquinone is converted to ethyl anthrahydroquinone.

EXAMPLE 6

$H_2S$ and t-butyl anthraquinone are dissolved in n,n-dimethylformamide solvent and reacted under the same conditions as Example 5. About 44% of the t-butyl anthraquinone is converted to t-butyl anthrahydroquinone. The higher conversion of the anthraquinone to anthrahydroquinone in Example 6 compared to Example 5 is attributed to the presence of the t-butyl group on the anthraquinone. The t-butyl group makes the anthraquinone more electronegative, enabling it to more effectively attract hydrogen ions from the quaternary ion complex formed between the $H_2S$ and the n,n-dimethylformamide solvent.

Examples 7-8 describe selection of the catalyst metal composition and catalyst support used in the dehydrogenation reactor.

EXAMPLE 7 t-Butyl anthrahydroquinone is converted to the corresponding anthraquinone and anthrone in a dehydrogenation reactor. Several catalyst supports are tested with nickel (Ni) and nickel-tungsten (Ni-W) catalyst metal compositions. Stainless steel (316) is the reactor material for the catalytic reaction studies. For comparison, thermal dehydrogenation reactions are also carried out in copper and mild steel reactors. The solvent is NMP, the hydrogen pressure is between 83 and 462 kPa, and the residence time is 1.5 to 4.9 minutes in all the catalytic and thermal tests. Table 4 shows the selectivity of the catalyst supports for converting t-butyl anthrahydroquinone to the corresponding anthraquinone at the temperature at which 100% of the anthrahydroquinone is converted to anthraquinone or anthrone.

TABLE 4

| Catalyst Metal Composition (wt. %) | Catalyst Support | Temperature (°C.) | % Selectivity to Anthraquinone |
| --- | --- | --- | --- |
| 6% Ni - 19% W | Silica-Alumina | 237 | 81 |
| 8.3% Ni | Silica | 293 | 91 |
| 3% Ni - 23% W | Alumina | 293 | 91 |
| 50% Ni | Alumina | 293 | 91 |
| 3.4% Ni | MgO | 293 | 91 |
| Ni pellets | None | 293 | 91 |
| None - Copper Reactor | None | 324 | 90 |
| None - Mild Steel Reactor | None | 324 | 90 |

The silica-alumina support, having a relatively high Bronsted acidity, attains 100% conversion of the t-butyl anthrahydroquinone at the lowest temperature, 237° C. However, the selectivity of the catalyst support to the anthraquinone is only 81%. Although the more basic supports (silica, alumina and magnesium oxide) require a higher temperature, 293° C., to attain 100% conversion, they yield a significantly higher selectivity to the anthraquinone of 91%. Noncatalytic thermal dehydrogenation is 90% selective to the anthraquinone, but requires a temperature of 324° C. to attain 100% conversion.

EXAMPLE 8 t-Butyl anthrahydroquinone is converted to the corresponding anthraquinone and anthrone in a dehydrogenation reactor. Several catalyst compositions with alumina supports are tested. The reactions are carried out in an NMP solvent at a hydrogen pressure of 83 kPa. The reactor is 316 stainless steel and the residence time is between 1 and 5 minutes. Table 5 shows the selectivity of the catalysts for converting t-butyl anthrahydroquinone to the corresponding anthraquinone at the temperature at which 100% of the anthrahydroquinone is converted to anthraquinone or anthrone.

TABLE 5

| Catalyst Metal Composition (wt. %) | Catalyst Support | Temperature (°C.) | % Selectivity to Anthraquinone |
| --- | --- | --- | --- |
| 20% $Cr_2O_3$ | Alumina | 272 | 93 |
| $P_r$-Re | Alumina | 280 | 91 |
| 2.4% Co - 9.9% Mo | Alumina | 272 | 91 |
| 50% Ni | Alumina | 293 | 91 |

Chromium oxide ($Cr_2O_3$) has the highest selectivity, 93%, to t-butyl anthraquinone. A probable explanation is that $Cr_2O_3$ is either a p-type conductor or an electron-attracting material.

While the foregoing preferred embodiments of the invention have been described and shown, it is understood that all alternatives and modifications, such as those suggested and others, may be made thereto and fall withing the scope of the invention.

We claim:

1. A process for converting hydrogen sulfide gas to sulfur and hydrogen gas comprising the steps of:
   (a) contacting said hydrogen sulfide gas with an anthraquinone dissolved in a polar organic solvent;
   (b) reacting said hydrogen sulfide gas with said anthraquinone to produce said sulfur and an anthrahydroquinone in said solvent;
   (c) separating said sulfur from said solvent;
   (d) dehydrogenating said anthrahydroquinone at a temperature of about 200° to about 350° C. to produce hydrogen gas and to regenerate said anthraquinone in said solvent; and
   (e) recycling said anthraquinone in said solvent to step (a).

2. The process of claim 1 wherein the polarity of said solvent is greater than 3 Debye units.

3. The process of claim 1 wherein said anthraquinone is t-butyl anthraquinone or ethyl anthraquinone.

4. The process of claim 1 wherein the reaction of step (b) is at a temperature from about 30° to 80° C.

5. The process of claim 1 wherein the reaction of step (b) is at a hydrogen sulfide partial pressure from 600 to about 1200 kPa.

6. The process of claim 1 wherein the dehydrogenation of step (d) is at a pressure from about atmospheric pressure to about 1000 kPa.

7. The process of claim 1 wherein the dehydrogenation of step (d) is thermal.

8. The process of claim 1 wherein the dehydrogenation of step (d) is catalytic.

9. The process of claim 8 wherein an electron-attracting catalyst metal catalyzes the dehydrogenation of step (d).

10. The process of claim 8 wherein chromium oxide catalyzes the dehydrogenation of step (d).

11. The process of claim 8 wherein the catalyst has a basic catalyst support.

12. The process of claim 11 wherein said catalyst support is alumina or magnesium oxide.

13. The process of claim 1 further comprising the step of flashing substantially any hydrogen sulfide remaining in said solvent after step (c) by heating said solvent to the dehydrogenation temperature.

14. The process of claim 2 wherein said solvent is n-methyl-2-pyrrolidone.

15. A process for converting hydrogen sulfide gas to sulfur and hydrogen gas comprising the steps of:
    (a) contacting said hydrogen sulfide gas in a feed gas, comprised of said hydrogen sulfide and at least one substantially unreactive constituent with an anthraquinone dissolved in a polar organic solvent;
    (b) reacting said hydrogen sulfide with said anthraquinone to produce said sulfur and an anthrahydroquinone in said solvent;
    (c) separating said sulfur from said solvent;
    (d) dehydrogenating said anthrahydroquinone at a temperature of about 200° to about 350° C. to produce hydrogen gas and to regenerate said anthraquinone in said solvent; and
    (e) recycling said anthraquinone in said solvent to step (a).

16. The process of claim 15 wherein the polarity of said solvent is greater than 3 Debye units.

17. The process of claim 15 wherein said anthraquinone is t-butyl anthraquinone or ethyl anthraquinone.

18. The process of claim 15 wherein the reaction of step (b) is at a temperature from about 30° to 80° C.

19. The process of claim 15 wherein the reaction of step (b) is at a hydrogen sulfide partial pressure of from about 600 to about 1200 kPa.

20. The process of claim 15 wherein the dehydrogenation of step (d) is at a pressure from about atmospheric pressure to about 1000 kPa.

21. The process of claim 15 wherein the dehydrogenation of step (d) is thermal.

22. The process of claim 15 wherein the dehydrogenation of step (d) is catalytic.

23. The process of claim 22 wherein an electron-attracting catalyst metal catalyzes the dehydrogenation of step (d).

24. The process of claim 22 wherein chromium oxide catalyzes the dehydrogenation of step (d).

25. The process of claim 22 wherein the catalyst has a basic catalyst support.

26. The process of claim 25 wherein said catalyst support is alumina or magnesium oxide.

27. The process of claim 15 further comprising the step of flashing substantially any hydrogen sulfide and at least one substantially unreactive constituent remaining in said solvent after step (c) by heating said solvent to the dehydrogenation temperature.

28. The process of claim 16 wherein said solvent is n-methyl-2-pyrrolidone.

* * * * *